(12) United States Patent
Choi et al.

(10) Patent No.: US 10,188,841 B2
(45) Date of Patent: Jan. 29, 2019

(54) CAPSULE-TYPE MICROROBOT AND USING METHOD THEREOF

(71) Applicant: Daegu Gyeongbuk Institute of Science and Technology, Daegu (KR)

(72) Inventors: Hong Soo Choi, Daegu (KR); Sang Won Kim, Daegu (KR); Seung Min Lee, Gyeongsangbuk-do (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 0 days.

(21) Appl. No.: 14/735,901

(22) Filed: Jun. 10, 2015

(65) Prior Publication Data
US 2015/0351856 A1 Dec. 10, 2015

(30) Foreign Application Priority Data
Jun. 10, 2014 (KR) .................. 10-2014-0070347

(51) Int. Cl.
*A61B 19/00* (2006.01)
*A61M 31/00* (2006.01)
(Continued)

(52) U.S. Cl.
CPC ....... *A61M 31/002* (2013.01); *A61B 1/00156* (2013.01); *A61B 5/6861* (2013.01); *A61B 17/00234* (2013.01); *A61B 34/30* (2016.02); *A61B 34/35* (2016.02); *A61B 1/041* (2013.01); *A61B 5/07* (2013.01); *A61B 2017/00004* (2013.01); *A61B 2017/00345* (2013.01);
(Continued)

(58) Field of Classification Search
CPC ............ A61K 9/0068; A61M 37/0069; A61B 1/00158; A61B 2017/00345; A61B 2019/2219; A61B 2019/2257
See application file for complete search history.

(56) References Cited

U.S. PATENT DOCUMENTS 4,564,363 A * 1/1986 Bagnall .................... A61D 7/00
222/641
4,662,879 A * 5/1987 Drake .................. A61K 9/0068
424/438

(Continued)

OTHER PUBLICATIONS

F. Munoz, G. Alici and W. Li, "A magnetically actuated drug delivery system for robotic endoscopic capsules," Journal of Medical Devices, vol. 10, No. 1, pp. 1-11, 2016.*

(Continued)

*Primary Examiner* — Nathan R Price
*Assistant Examiner* — Justin L Zamory
(74) *Attorney, Agent, or Firm* — Masuvalley & Partners (57) ABSTRACT

A capsule-type microrobot is provided. A capsule-type microrobot according to the present invention comprises a motor including a receptacle having an internal space, with one portion thereof being open, a body extending from the receptacle, and a magnetic layer disposed on an outer surface of the body. A cap is coupled to a predetermined portion of the receptacle to close the internal space such that contents are contained in the receptacle. The motor separates the cap therefrom by rotating with respect to the cap through an interaction between a rotating magnetic force applied from an external source and the magnetic layer, whereby the contents are discharged from the receptacle.

6 Claims, 9 Drawing Sheets

(51) Int. Cl.
| | |
|---|---|
| A61B 5/00 | (2006.01) |
| A61B 17/00 | (2006.01) |
| A61B 34/30 | (2016.01) |
| A61B 34/35 | (2016.01) |
| A61B 1/00 | (2006.01) |
| A61B 34/00 | (2016.01) |
| A61B 1/04 | (2006.01) |
| A61B 5/07 | (2006.01) |

(52) U.S. Cl.
CPC ... *A61B 2034/303* (2016.02); *A61B 2034/731* (2016.02); *A61B 2562/028* (2013.01)

(56) References Cited

U.S. PATENT DOCUMENTS

| | | | | |
|---|---|---|---|---|
| 6,240,312 | B1* | 5/2001 | Alfano | A61B 1/00016 128/903 |
| 6,292,678 | B1* | 9/2001 | Hall | A61M 25/0127 600/374 |
| 2004/0210128 | A1* | 10/2004 | Martel | A61B 1/00156 600/411 |
| 2008/0033569 | A1* | 2/2008 | Ferren | A61B 34/20 623/23.7 |
| 2008/0214894 | A1* | 9/2008 | Wedel | A61B 1/00158 600/118 |
| 2011/0166416 | A1* | 7/2011 | Katayama | A61B 1/00082 600/104 |
| 2011/0304717 | A1* | 12/2011 | Degenhardt | A61B 1/00158 348/65 |
| 2013/0303847 | A1* | 11/2013 | Sitti | A61B 1/00158 600/104 |

OTHER PUBLICATIONS

L. Zhang, J. J. Abbott, L. Dong, B. E. Kratochvil, D. Bell and B. J. Nelson, "Artifical bacterial flagella: Fabrication and magnetic control," Applied Physics Letters, p. 94, 2009.*

A. W. Mahoney and J. J. Abbott, "Generating Rotating Magnetic Fields With a Single Permanent Magnet for Propulsion of Untethered Magnetic Devices in a Lumen," IEEE Transactions on Robotics, vol. 30, No. 2, pp. 411-420, 2014.*

S. M. Jeon, G. H. Jang, H. C. Choi, S. H. Park and J. O. Park, "Magnetic navigation system for the precise helical and translational motions of a microrobot in human blood vessels," Journal of Applied Physics, vol. 111, pp. 07E702-07E702-3, 2012.*

F. Qiu, S. Fujita, R. Mhanna, L. Zhang, B. R. Simona and B. J. Nelson, "Magnetic Helical Microswimmers Functionalized with Lipoplexes for Targeted Gene Delivery," Adv. Funct. Mater., vol. 25, pp. 1666-1671, 2015.*

T. W. R. Fountain, P. V. Kailat and J. J. Abbott, "Wireless Control of Magnetic Helical Microrobots using a Rotating-Permanent-Magnet Manipulator," in IEEE International Conference on Robotics and Automation, Anchorage, 2010.*

Kummer, Michael P. et al., "OctoMag: An Electromagnetic System for 5-DOF Wireless Micromanipulation," *IEEE Transactions on Robotics*, vol. 260, No. 6, Dec. 2010, pp. 1006-1017, 12 pages.

Peyer, Katherin E. et al., "Bio-inspired magnetic swimming microrobots for biomedical applications," *Nanoscale*, 2013, Issue 5, Mar. 7, 2013, pp. 1259-1272, 14 pages.

* cited by examiner

FIG. 8

CAPSULE-TYPE MICROROBOT AND USING METHOD THEREOF

CROSS REFERENCE TO RELATED APPLICATION

The present application claims priority from Korean Patent Application Number 10-2014-0070347 filed on Jun. 10, 2014, the entire contents of which are incorporated herein for all purposes by this reference.

BACKGROUND OF THE INVENTION

Field of the Invention

The present invention relates to a capsule-type microrobot and a using method thereof. More particularly, the present invention relates to a capsule-type microrobot and a using method thereof, in which the microrobot has a magnetic layer and can operate in response to a magnetic field applied from an external source in order to discharge a medicine.

Description of Related Art

The lifespan of humans has increased with advancements in medicine and science. However, a variety of intractable diseases, such as cancer, as well as tissue injuries caused by accidents are increasing on a day by day basis.

In order to treat such intractable diseases and tissue injuries, microrobotics, i.e. a branch of robotics dealing with microrobots having a diameter of 1 mm or less, has recently been developed. Specifically, a microrobot may be inserted into a human body in order to observe and diagnose the interior of a blood vessel, brain tissue, or a localized portion of the human body, as well as perform a treatment and operations on such portions of the human body.

A typical microrobot of the related art includes a driving part performing a task, a sensor detecting a target point, a power supply supplying power to the driving part, and a radio transceiver transmitting signals to and receiving signals from an external device. Such microrobots have been developed with a focus on the functions of locating cancer cells and observing damaged tissue.

In the related art, a medicine must be directly injected to a target portion of the human body by surgical intervention or the assistance of a machine in order to treat the observed cancer cells or the injured tissue. This may cause a problem in that a portion of the human body, such as a localized portion thereof, a blood vessel, or brain tissue, must be exposed to the outside of the body.

In order to overcome such problems, Korean Patent Application Publication No. 10-2010-0048728 (published on May 11, 2010) disclosed "MICROROBOT CAPABLE OF TRACING AND CURING OF LESIONS BY USING BACTERIA, AN OPERATING METHOD THEREOF, AND A TREATING METHOD THEREOF."

Figure 1:
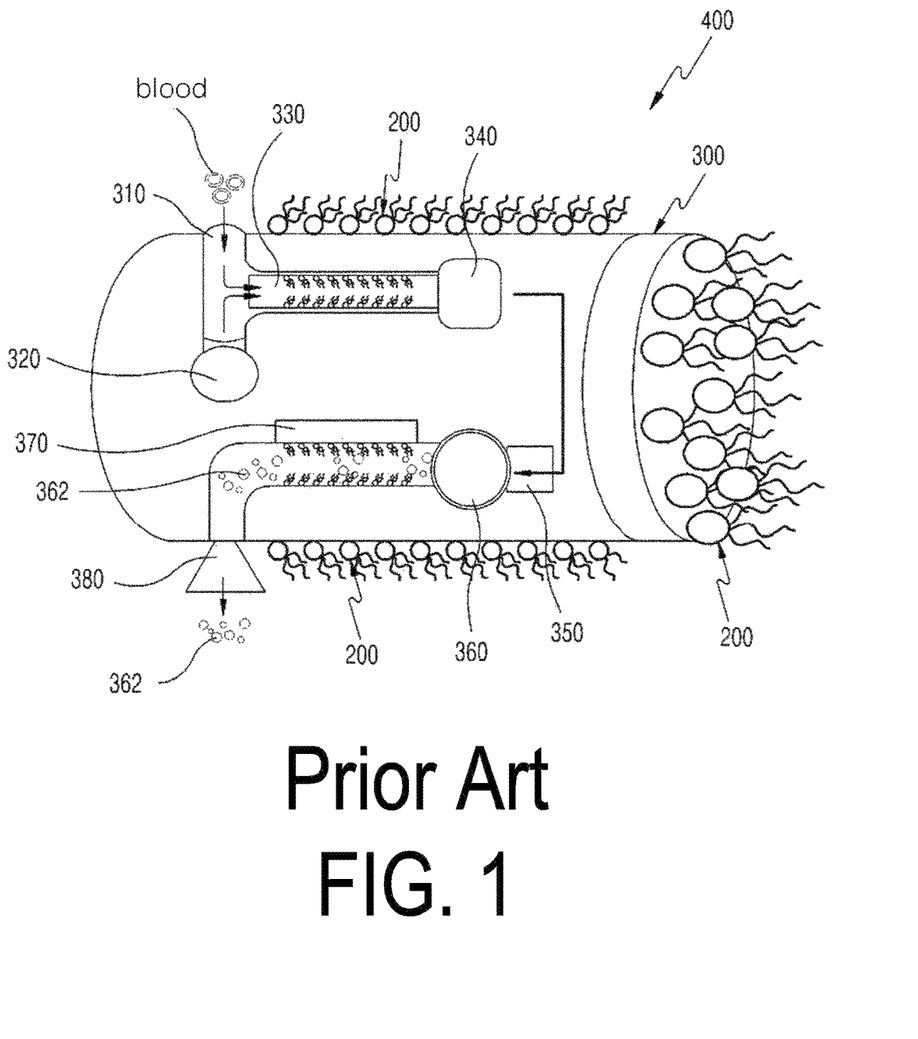
FIG. 1 illustrates a microrobot using bacteria of the related art.
Figure 2:
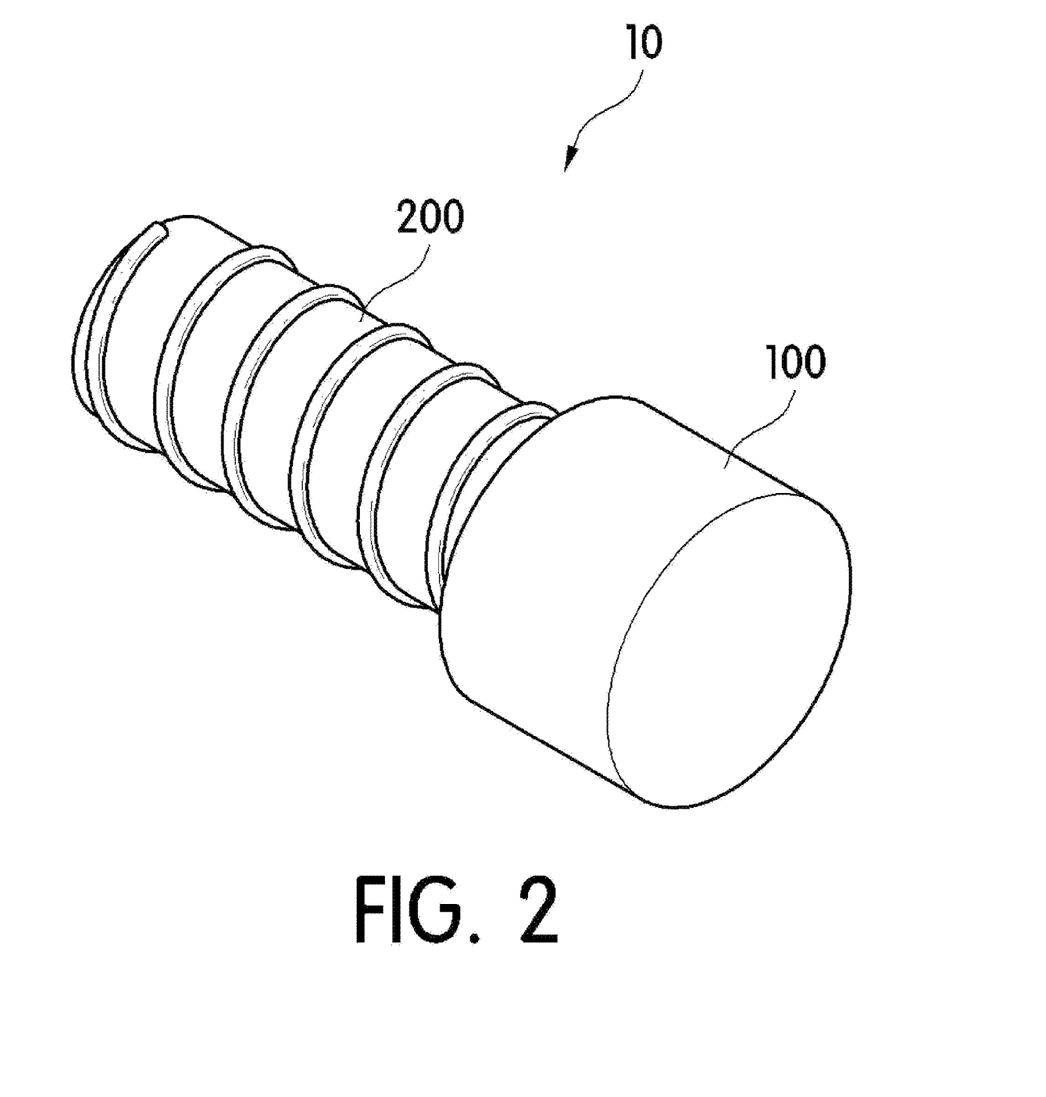
FIG. 2 is a perspective view illustrating a first embodiment of a motor of a capsule-type microrobot according to an exemplary embodiment of the present invention.

As illustrated in FIG. 1, the microrobot using bacteria of the related art includes a capsule-shaped microstructure 300 containing a specific medicine and bacteria 200 having flagella. The bacteria 200 are designed to locate cancer cells by detecting a specific substance (e.g., a stimulator) secreted from the cancer cells.

However, since the microrobot using bacteria locates a target by detecting a specific substance secreted from cancer cells, it is difficult to design such a microrobot using bacteria to locate tissues or cells from which no specific substance is secreted.

The information disclosed in the Background of the Invention section is only provided for better understanding of the background of the invention and should not be taken as an acknowledgment or any form of suggestion that this information forms prior art that would already be known to a person skilled in the art.

RELATED ART DOCUMENT

Patent Document 1: Korean Patent Application Publication No. 10-2010-0048728 (May 11, 2010)

BRIEF SUMMARY OF THE INVENTION

Various aspects of the present invention provide a capsule-type microrobot that has superior biocompatibility and can precisely move to a target point in response to a magnetic field applied from an external source.

Also provided is a capsule-type microrobot able to decouple a cap from a motor in response to a magnetic field applied from an external source, thereby discharging contents of the receptacle externally from the receptacle.

In an aspect of the present invention, a capsule-type microrobot includes: a motor comprising a receptacle having an internal space, with one portion thereof being open, a body extending from the receptacle, and a magnetic layer disposed on an outer surface of the body; and a cap coupled to a predetermined portion of the receptacle to close the internal space such that contents are contained in the receptacle. The motor separates the cap therefrom by rotating with respect to the cap through an interaction between an rotating magnetic force applied from an external source and the magnetic layer, whereby the contents are discharged from the receptacle.

According to an embodiment of the present invention, the magnetic layer may be disposed on a portion of the body.

The cap may include a resin body formed of resin and a protective layer covering the resin body, the protective layer being formed of a biocompatible material.

The body of the motor may be formed of resin, the body having threads thereon or being a spiral body. The magnetic layer may be disposed on the body. The motor may further include a protective layer covering the magnetic layer, the protective layer being formed of a biocompatible material.

The motor and the resin body may be formed of a biocompatible material or a bio-inert material.

In another aspect of the present invention, provided is a method of using a capsule-type microrobot, wherein the microrobot includes: a motor including a receptacle having an internal space, with one portion thereof being open, a body extending from the receptacle, and a magnetic layer disposed on an outer surface of the body; and a cap coupled to a predetermined portion of the receptacle to close the internal space such that contents are contained in the receptacle. The method includes: inserting the microrobot into a human body in a state in which the cap is coupled to the motor; moving the microrobot to a preset target point of the human body by causing the motor coupled to the cap to rotate through interaction with a rotational magnetic field by applying the rotational magnetic field to the motor; and discharging the contents from the receptacle by separating the cap from the motor having the magnetic layer by applying a rotational magnetic field to the motor in the direction opposite to the rotational magnetic field applied in the step of moving the microrobot to the preset target point.

According to an embodiment of the present invention, the method may further include, before the step of inserting the microrobot into the human body: submerging the motor and the cap into a storage container in which the contents are stored; and coupling the predetermined portion of the motor to the cap by applying a rotational magnetic field to the motor, such that the contents are contained in the internal space of the receptacle.

The method may further include, after the step of discharging the contents from the receptacle, discharging the motor from the human body by applying a rotational magnetic field to the motor.

The method may further include, after the step of discharging the contents from the receptacle, coupling the motor to the cap by applying a rotational magnetic field to the motor, the rotational force of the rotational magnetic field being greater than the rotational force of the cap; and discharging the microrobot from the human body in a state in which the cap is coupled to the motor by applying a rotating magnetic field to the motor, the rotational force of the rotational magnetic field being smaller than the rotational force of the rotational magnetic field applied in the step of coupling the motor to the cap.

According to the present invention as set forth above, the following effects may be realized:

(1) The superior biocompatibility of the capsule-type microrobot can prevent side effects during the process of insertion of the capsule-type microrobot into the human body and during the use therein.

(2) It is possible to discharge the contents for treatment by separating the cap from the receptacle in which the contents are contained while controlling the movement of the microrobot using a rotational magnetic field applied from an external source. Accordingly, it is possible to directly discharge the contents to a localized portion of the human body, a blood vessel, or brain tissue without surgical intervention or the assistance of a machine.

The methods and apparatuses of the present invention have other features and advantages that will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to various embodiments of the present invention in conjunction with the accompanying drawings so that a person skilled in the art to which the present invention relates could easily put the present invention into practice. In the following detailed description of the structural principle of exemplary embodiments of the present invention, detailed descriptions of known functions and components incorporated herein will be omitted in the case that the subject matter of the present invention is rendered unclear.

Reference should be made to the drawings, in which the same reference numerals and symbols will be used throughout the different drawings to designate the same or like components.

In addition, throughout this document, when an element is referred to as being "connected to" or "coupled to" another element, not only it can be "directly connected" or "coupled to" the other element, but also it can be "indirectly connected or coupled to" the other element via an "intervening" element. Furthermore, it will be understood that the terms "comprise," "include," "have," and any variations thereof used herein are intended to cover a non-exclusive inclusion unless explicitly described to the contrary.

A capsule-type microrobot 10 according to an exemplary embodiment of the present invention is inserted into an interior of a human body, such as an interior of a blood vessel, as well as a localized portion of the human body, such as brain tissue or an eyeball, in order to discharge cells or a medicine to a target point of the human body. It is possible to fabricate the capsule-type microrobot 10 having a microscale three-dimensional structure from a photocurable polymer by lithography. Due to having a microscopic size, the capsule-type microrobot 10 can easily move within a living body.

Referring to FIG. 2 to FIG. 7, the capsule-type microrobot 10 according to the present exemplary embodiment includes a motor 200 and a cap 100.

Figure 4:
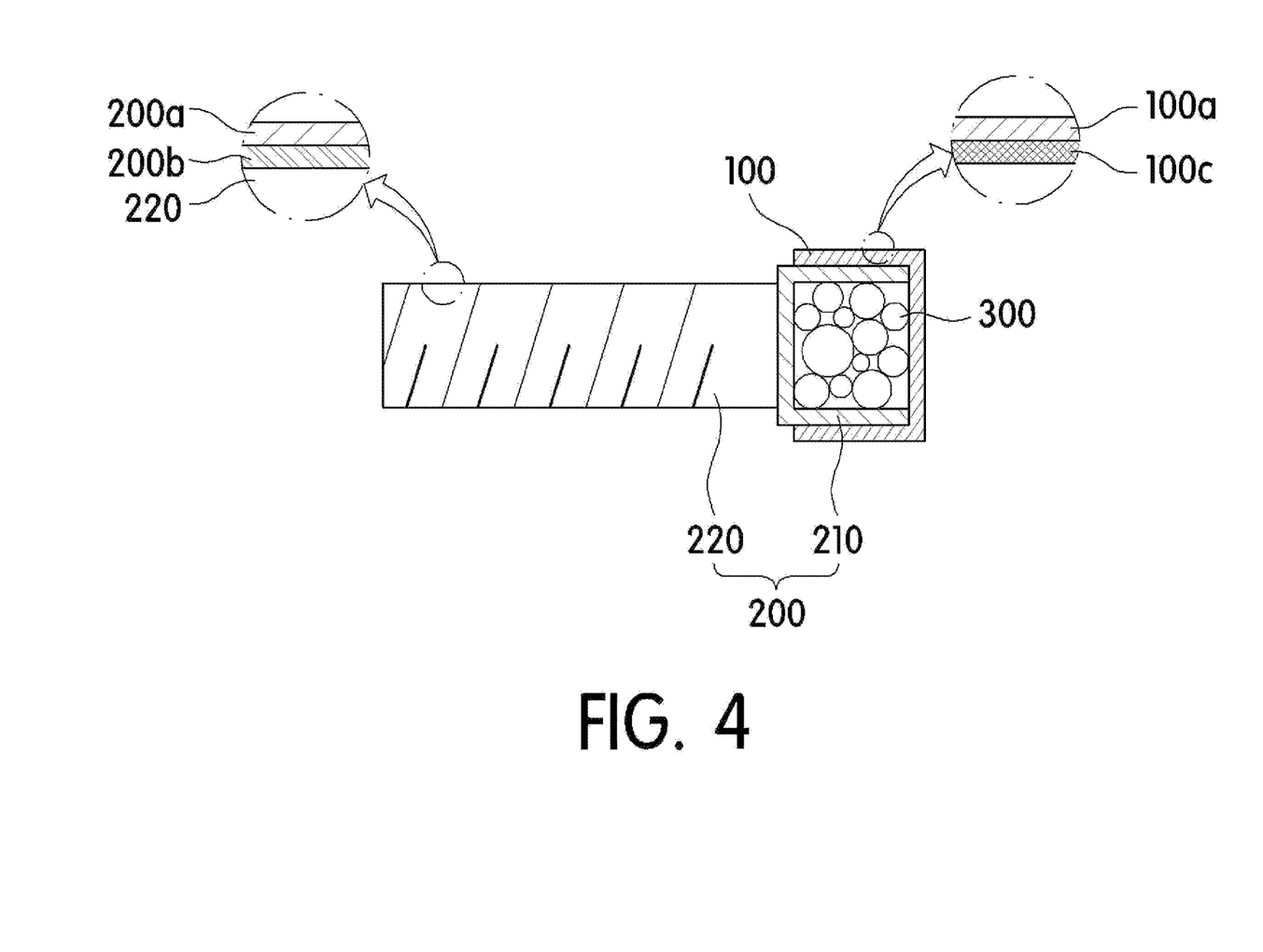
FIG. 4 is an enlarged view illustrating the capsule-type microrobot according to the exemplary embodiment of the present invention.

Referring to FIG. 4, the motor 200 has a receptacle 210 containing contents 300. The receptacle 210 has an internal space, with one portion thereof being open, such that contents 300 can be contained within the receptacle 210. The motor 200 also has a body 220 extending for a predetermined length from the receptacle 210. Threads having a predetermined pitch are formed on the outer surface of the body 220.

The body 220 is a cylindrical body formed of resin, and has a magnetic layer 200b disposed on the entire outer surface thereof, including on the threads, such that the body 220 can rotate in response to a rotational magnetic field applied from an external source.

Figure 3:
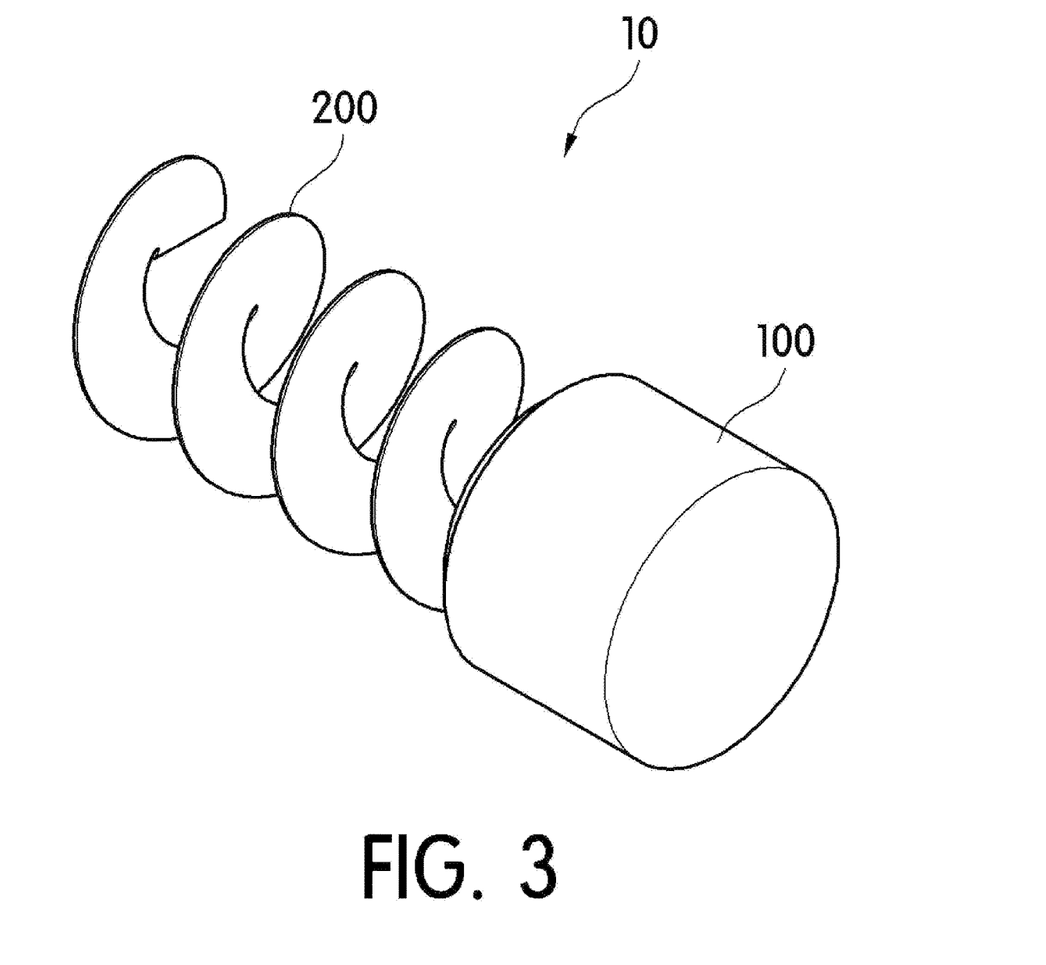
FIG. 3 is a perspective view illustrating a second embodiment of the motor of the capsule-type microrobot according to the exemplary embodiment of the present invention.

However, this is not intended to be limiting. As illustrated in FIG. 3, the body 220 may be implemented as a spiral body formed of resin, and the magnetic resin 200b may be disposed on the entire outer surface of the body 220 such that the body 220 can rotate in response to a rotational magnetic field applied from an external source.

The magnetic layer 200b is formed of a magnetic metal, the degree of corrosiveness (reactivity) of which is insignificant. It is preferable that the metal composition of the magnetic layer 200b be one selected from among nickel (Ni), iron (Fe), cobalt (Co), and neodymium (Nd), or mixtures thereof. It is more preferable that the metal composition contain Ni.

Although the magnetic layer 200b has been illustrated and described as being formed on the entire outer surface of the body, this is not intended to be limiting, and the magnetic layer may be formed on part of the outer surface of the body.

It is preferable that a protective layer 200a be added on the outer surface of the magnetic layer 200b in order to cover the magnetic layer 200b.

The cap 100 is coupled to one portion of the receptacle 210 to close the receptacle 210 in order to prevent the contents 300 of the receptacle from being discharged. The weight of the cap 100 may be greater than the weight of the motor 200 in order to facilitate the relative rotation of the motor 200.

Figure 5:
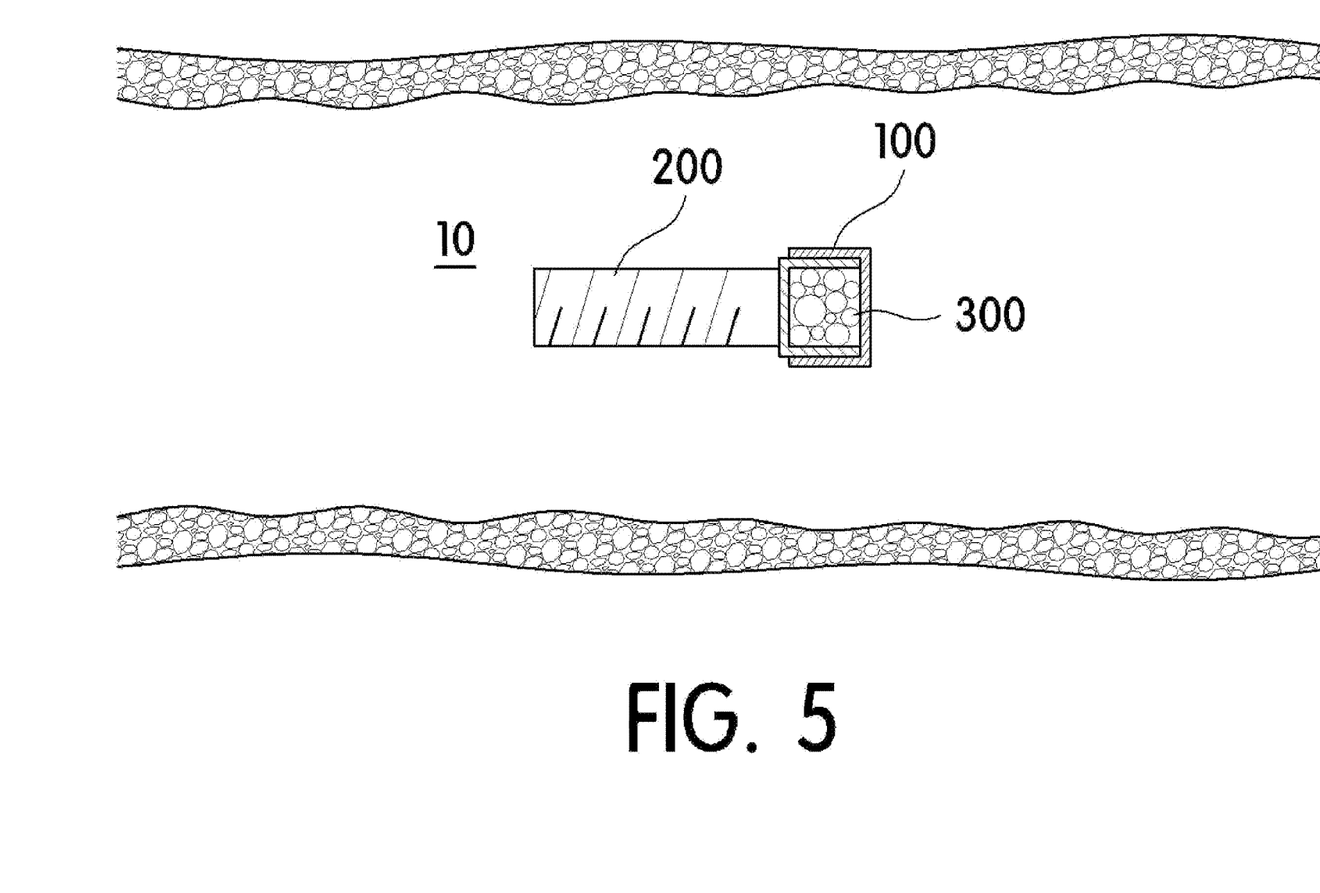
FIG. 5 illustrates the state in which the capsule-type microrobot according to the exemplary embodiment of the present invention is used.

FIG. 5 illustrates the state in which the capsule-type microrobot according to the present exemplary embodiment is used.

The capsule-type microrobot 10 is inserted into a human body using an endoscope (not shown) such that contents including a curative medicine can be absorbed by the human body. The capsule-type microrobot 10 is required to cause no side effect.

Accordingly, in order to prevent side effects in vivo, the motor 200 has the protective layer 200a, and the cap 100 has a protective layer 200a, the protective layers 100a and 200a covering the entire outer surfaces of the cap 100 and the motor 200.

It is preferable that the protective layers 100a and 200a be formed of a material having superior biocompatibility. The material may be one selected from among titanium (Ti), medical grade stainless steel, alumina ($Al_2O_3$), and gold (Au), or mixtures thereof. It is preferable that the material contain Ti.

It is preferable that the motor 200 including the body 220 and the receptacle 210 as well as a resin body 100c be formed of a biocompatible and biodegradable material such that the motor 200 and the resin body 100c can be biologically decomposed within the human body.

However, this is not intended to be limiting, and the motor 200 including the body 220 and the receptacle 210 and the resin body 100c may be formed of one or more selected from a biocompatible material, a bio-degradable, a bio-adhesive, and a bio-inert material.

Figure 6:
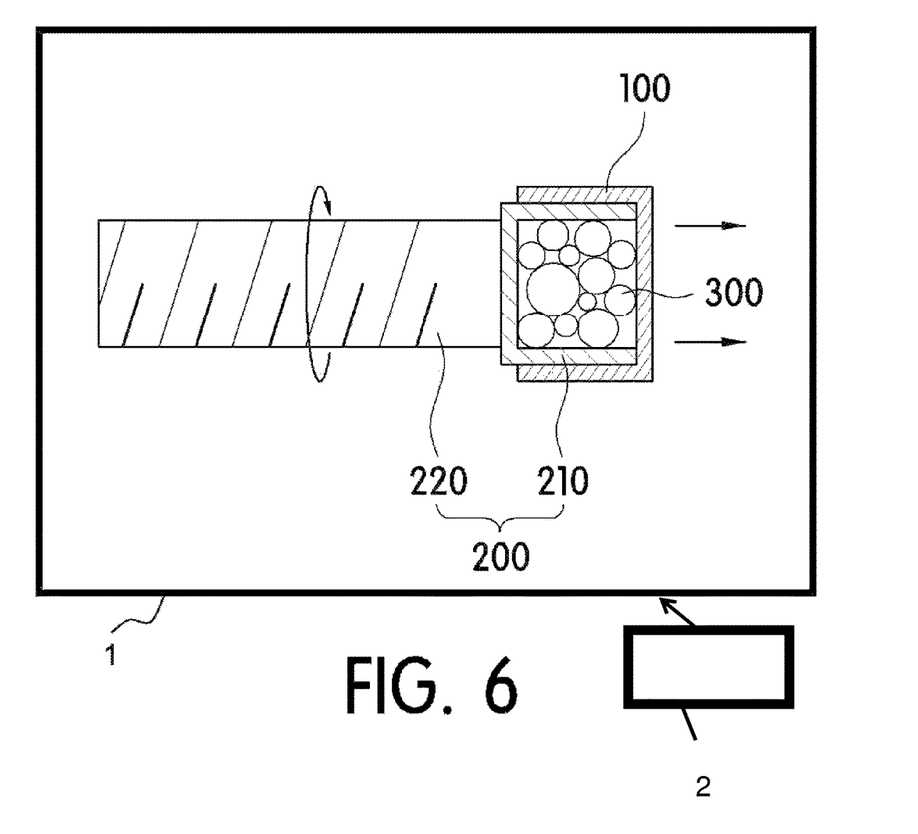
FIG. 6 illustrates a first operating state of the capsule-type microrobot according to the exemplary embodiment of the present invention.

FIG. 6 illustrates a first operating state of the capsule-type microrobot according to the exemplary embodiment of the present invention.

When a rotational magnetic field from an external source 2 is applied to the motor 200, the motor 200 having the magnetic layer 200 b rotates in the direction in which the rotational magnetic field is applied, in the state in which the motor 200 is coupled to the cap 100. Consequently, thrust caused by the rotation of the body on which the magnetic layer 200 b is formed causes the motor 200 to move horizontally in a single direction.

Accordingly, the cap 100 coupled to the motor 200 can arrive at a preset target point of the human body under the control of the rotational magnetic field.

Figure 7A:
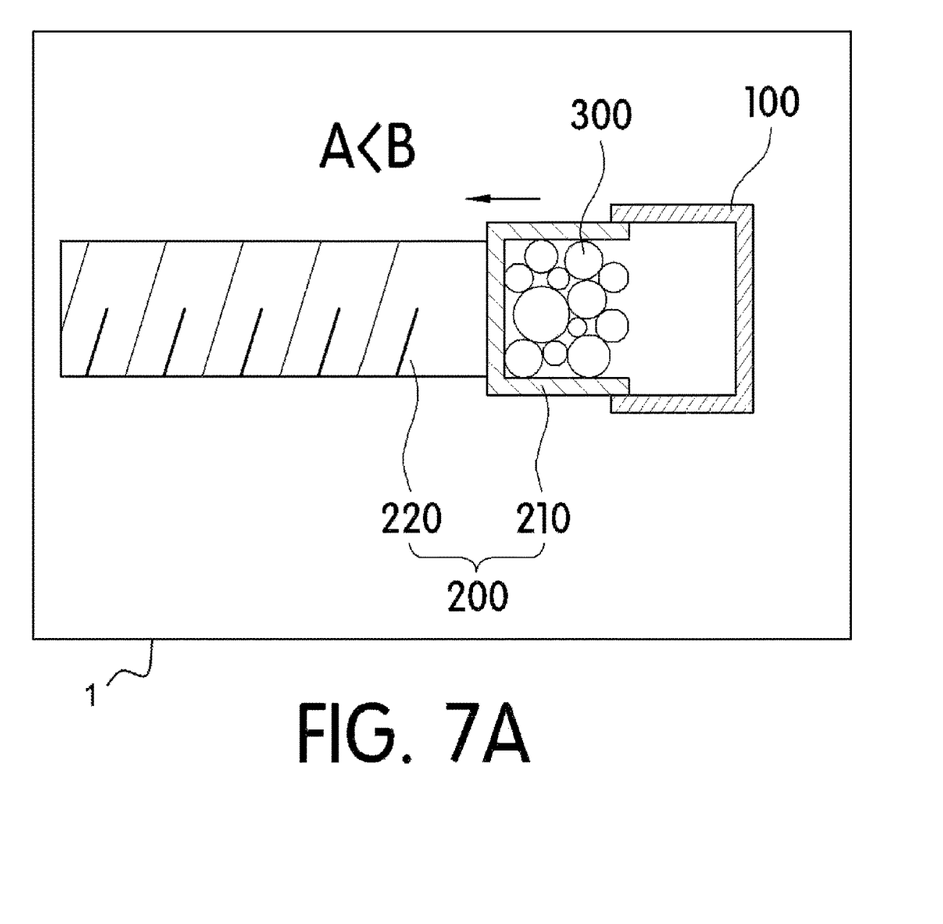
FIG. 7A and FIG. 7B illustrate a second operating state of the capsule-type microrobot according to the exemplary embodiment of the present invention.
Figure 7B:
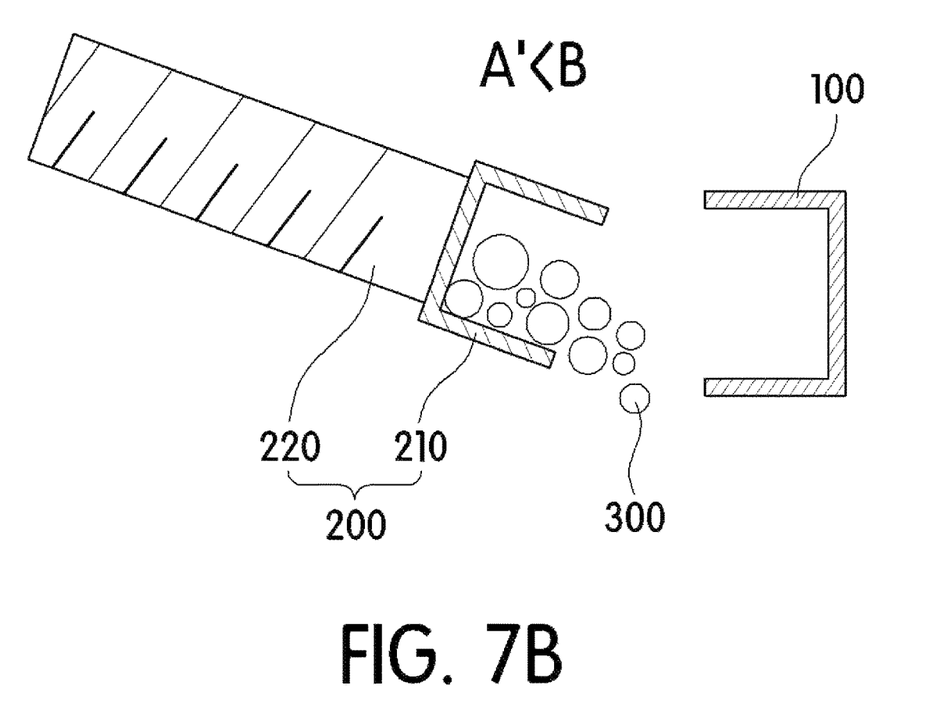

FIG. 7A and FIG. 7B illustrate a second operating state of the capsule-type microrobot according to the exemplary embodiment of the present invention.

As illustrated in FIG. 7A and FIG. 7B, in order to discharge the contents 300 from the receptacle 210, a rotational magnetic field 1 applied to the motor 200 is increased such that the rotational force of the motor 200 becomes greater than the rotational force of the cap 100. Since the rotational force of the motor 200 to which the receptacle 210 is coupled becomes greater than the rotational force of the cap 100, the cap 100 is separated from the receptacle 210.

Consequently, the contents 300 of the receptacle 210 are discharged to the target point.

Reference will now be made to a using method of the capsule-type microrobot configured as above.

Figure 8:
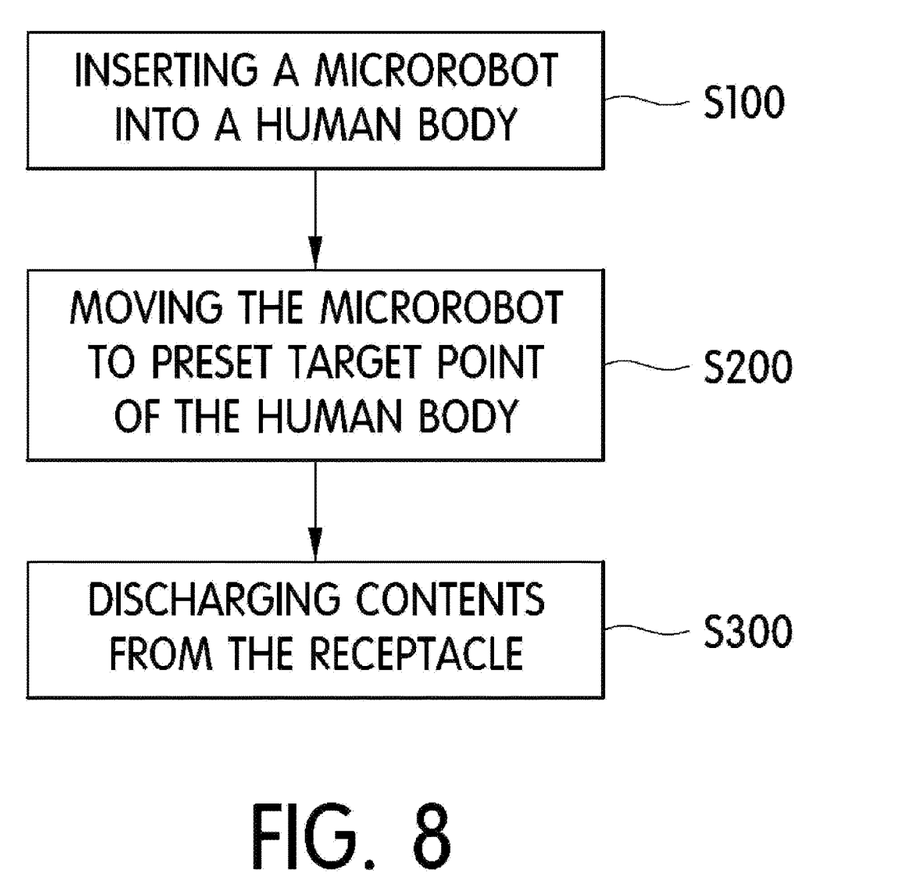
FIG. 8 is a flowchart illustrating a using method of the capsule-type microrobot according to the exemplary embodiment of the present invention.

FIG. 8 is a flowchart illustrating a using method of the capsule-type microrobot according to the present exemplary embodiment. Referring to FIG. 8, the using method of the capsule-type microrobot includes inserting the microrobot into a human body 5100, moving the microrobot to a preset target point of the human body 5200, and discharging the contents from the receptacle 5300.

At a step of inserting the microrobot into a human body 5100, the capsule-type microrobot 10, including the motor 200 and the cap 100 coupled to each other, is inserted into a human body using a device, such as an endoscope (not shown), or by being orally ingested in a pill.

Afterwards, at a step of moving the microrobot to a preset target point of the human body 5200, the capsule-type microrobot 10 moves to the target point of the human body where the contents 300 including a medicine or cells are to be injected. Specifically, a rotational magnetic field is applied to the capsule-type microrobot 10 inserted into the human body, and the motor 200 having the magnetic layer 200b rotates together with the cap 100 through interaction with the rotational magnetic field, thereby moving to the preset target point.

Thereafter, at a step of discharging the contents from the receptacle 5300, the capsule-type microrobot 10 that has arrived at the target point discharges the contents 300 contained therein. Specifically, a rotational magnetic field in the direction opposite to the external magnetic field applied for the movement is applied to the motor 200 that has arrived at the target point, such that the threaded or spiral motor 200 having the magnetic layer 200b is separated from the cap 100 that does not have a magnetic layer, thereby discharging the contents 300 of the receptacle 210 externally from the receptacle.

Accordingly, it is possible to discharge the contents 300 to the target point by controlling the rotational magnetic field supplied from the external source without surgical intervention or the assistance of a machine unlike the related art. The target point may be a localized portion of the human body, a blood vessel, or brain tissue, the exposure of which externally from the human body may be fatal.

It is preferable that the step of preparing and the step of coupling motor be carried out before the step of inserting the microrobot into a human body 5100. The step of preparing is submerging the motor 200 and the cap 100 into a storage container in which the contents 300 are stored is performed. The step of coupling motor is coupling one portion of the motor 200 to the cap 100 by applying a rotational magnetic field to the motor 200 submerged in the storage container.

It is preferable that the method further include a step of discharging the motor 200 from the human body by applying a rotating magnetic force to the motor 200 after the step of discharging the contents from the receptacle 5300. In this case, the cap 100 may be formed of a biodegradable material that can be decomposed within the human body.

The capsule-type microrobot according to the present invention having superior biocompatibility can prevent side effects during the insertion and use thereof into and in the human body. It is possible to control the movement of the microrobot and separate the cap from the receptacle containing the contents therein using rotational magnetic fields applied from the external source, thereby directly discharging the contents to a localized portion of the human body, a blood vessel, or brain tissue without surgical intervention or the assistance of a machine.

It should be understood that the present invention is not limited by the embodiments as set forth above and the drawings as attached. A person skilled in the art will appreciate that various substitutes, modifications, and changes are possible without departing from the scope and spirit of the invention.

What is claimed is:

1. A capsule-type microrobot comprising:
   a motor comprising a receptacle having an internal space, with one portion thereof being open, a body extending from the receptacle, and a magnetic layer disposed on an outer surface of the body; and
   a cap coupled to a predetermined portion of the receptacle to close the internal space such that contents are contained in the receptacle, the cap being of different weight than the motor,
   wherein the motor is magnetically-rotatable via a rotating magnetic force in a first direction so as to move the microrobot; and wherein the motor is magnetically-rotatable via the rotating magnetic force in a second direction so as to separate the cap from the motor, whereby the contents are discharged from the receptacle.

2. The capsule-type microrobot according to claim 1, wherein the magnetic layer is disposed on a portion of the body.

3. The capsule-type microrobot according to claim 1, wherein the cap comprises a resin body formed of resin and a protective layer covering the resin body, the protective layer being formed of one or more selected from a biocompatible material, a bio-degradable, a bio-adhesive, and a bio-inert material.

4. The capsule-type microrobot according to claim 3, wherein the motor and the resin body are formed of one or more selected from a biocompatible material, a bio-degradable, a bio-adhesive, and a bio-inert material.

5. The capsule-type microrobot according to claim 1, wherein the body of the motor is formed of resin, the body having threads thereon or comprising a spiral body, the magnetic layer is disposed on the body, and the motor further comprises a protective layer covering the magnetic layer, the protective layer being formed of one or more selected from a biocompatible material, a bio-degradable, a bio-adhesive, and a bio-inert material.

6. The capsule-type microrobot according to claim 5, wherein the motor and the resin body are formed of one or more selected from a biocompatible material, a bio-degradable, a bio-adhesive, and a bio-inert material.

* * * * *